United States Patent [19]

Iimuro et al.

[11] Patent Number: 4,942,265
[45] Date of Patent: Jul. 17, 1990

[54] PROCESS FOR PREPARING 2,2-BIS(4-HYDROXYPHENYL)PROPANE OF HIGH PURITY

[75] Inventors: Shigeru Iimuro; Takashi Kitamura, both of Nagoya; Yoshio Morimoto, Tokai, all of Japan

[73] Assignee: Mitsui Toatsu Chemicals, Inc., Tokyo, Japan

[21] Appl. No.: 276,809

[22] Filed: Nov. 28, 1988

[30] Foreign Application Priority Data

Dec. 4, 1987 [JP] Japan .................. 62-305941

[51] Int. Cl.$^5$ ................ C07C 37/70; C07C 39/16
[52] U.S. Cl. .................. 568/724; 568/727; 568/728; 568/750
[58] Field of Search ............ 568/724, 727, 728, 750

[56] References Cited

U.S. PATENT DOCUMENTS

| | | | |
|---|---|---|---|
| 3,049,569 | 8/1962 | Apel et al. | 568/728 |
| 3,221,061 | 11/1965 | Grover et al. | 568/728 |
| 4,492,807 | 1/1985 | Aneja | 568/724 |
| 4,798,654 | 1/1989 | Iimura et al. | 568/724 |

FOREIGN PATENT DOCUMENTS

| | | | |
|---|---|---|---|
| 51-91240 | 8/1976 | Japan | 568/724 |
| 52-42790 | 10/1977 | Japan | 568/724 |
| 59-62543 | 4/1984 | Japan | 568/728 |
| 59-231033 | 12/1984 | Japan | 568/724 |

*Primary Examiner*—Werren B. Lone
*Attorney, Agent, or Firm*—Burns, Doane, Swecker & Mathis

[57] ABSTRACT

The process for preparing 2,2-bis(4-hydroxyphenyl)-propane (bisphenol A) by reacting acetone with phenol and decomposing the resultant adduct of bisphenol A and phenol is well known. However, the quality of bisphenol A thus obtained is not always satisfactory.

In the process of this invention, the adduct is washed with phenol recovered by decomposing an adduct of bisphenol A and phenol, and then bisphenol A is prepared by decomposing the washed adduct.

The bisphenol A prepared by the process of this invention has an extremely high quality and is suitable for the preparation of polycarbonate used for optical parts.

5 Claims, 1 Drawing Sheet

PROCESS FOR PREPARING 2,2-BIS(4-HYDROXYPHENYL)PROPANE OF HIGH PURITY

BACKGROUND OF THE INVENTION

The present invention relates to a process for the preparation of 2,2-bis(4-hydroxyphenyl)propane (hereinafter also referred to as bisphenol A) of high purity.

Bisphenol A is used as a raw material for polycarbonate resins or epoxy resins. The demand for polycarbonate resins employed for optical parts in particular has recently increased. As a result, colorless and highly purified bisphenol A is required compared to conventional bisphenol A.

Bisphenol A is prepared by the reaction of acetone with excess phenol in the presence of an acid catalyst or a combination of an acid catalyst and a cocatalyst such as sulfur compounds. The reaction mixture contains, in addition to bisphenol A, catalyst, unreacted acetone, unreacted phenol, water and other by-products formed by the reaction.

Principal components of the by-products are 2-(2-hydroxyphenyl)-2-(4-hydroxyphenyl)propane, 2,2,4-trimethyl-4-(4-hydroxyphenyl)chroman, trisphenol, polyphenol and unfavorable colored substances. These by-products deteriorate the properties of the resin prepared from bisphenol A.

As to the process for preparing bisphenol A of high purity from a reaction mixture, utilization of an adduct of bisphenol A and phenol is a well known technique for those who are skilled in the art. For example, catalyst, water and a part of the phenol are removed from the reaction mixture and the remaining liquid is cooled to crystallize bisphenol A as the adduct with phenol. The crystals are separated from the mother liquor containing by-products of the reaction. Phenol is removed from the adduct to recover bisphenol A. Various methods such as distillation, extraction, steam stripping and the like have been proposed for removing phenol. For example, Societa Italiana Resine S.p.A. has disclosed a method for vaporizing the adduct for 0.1 to 30 minutes at a temperature higher than 180° C. under reduced pressure and fractionally condensing bisphenol [Japanese Patent Publication TOKKOSHO 52-42790 (1977)]. Mitsui Chemicals Co. has proposed a method for heating the adduct to 50° C. or above by using a solvent having a boiling point of higher than 50° C. to dissolve the phenol portion alone in the solvent [Japanese Patent Publication TOKKOSHO 36-23335 (1961)].

The intact bisphenol A obtained by those methods can be used as a raw material of common grade epoxy resins. The purity of the bisphenol A obtained by these methods, however, is insufficient for the preparation of polycarbonate. The crystals of adduct themselves contain impurities and thus bisphenol A obtained by removing phenol from the adduct has poor purity. Accordingly, further purification is needed in order to remove the impurities. For example, recrystallization from hot water is disclosed by Mitsui Petrochemicals Co. [Japanese Laid-Open Patent TOKKAISHO 59-62543 (1984)]. Washing by solvents is taught by General Electric Co. [Japanese Laid-Open Patent TOKKAISHO 59-231033 (1984)].

On the other hand, Union Carbide Corp. has disclosed a method for washing the adduct, which uses a mixture of phenol resulting from the decomposition of the adduct and fresh phenol externally supplied [Japanese Patent Publication TOKKOSHO 37-981 (1962) and 41-4454 (1966)]. No quantitative description, however, is found regarding the purity of the adduct obtained.

According to the examination by the present inventors, the hue of bisphenol A is not always satisfactory, even though its purity is acceptable. This is assumed to be due to the trace of washing liquid adhering to the resultant crystals of bisphenol A. As a result of further investigation, it has been found that commercial phenol can not provide satisfactory hue in the product bisphenol A, even though washing is repeated.

SUMMARY OF THE INVENTION

The object of this invention is to provide a process for preparing bisphenol A of high purity from the adduct of bisphenol A and phenol, which contains by-products of the reaction and impurities. The object can be favorably achieved in an industrial scale without using water or solvents which require complex procedures for recovery.

DETAILED DESCRIPTION OF THE INVENTION

Figure 1:
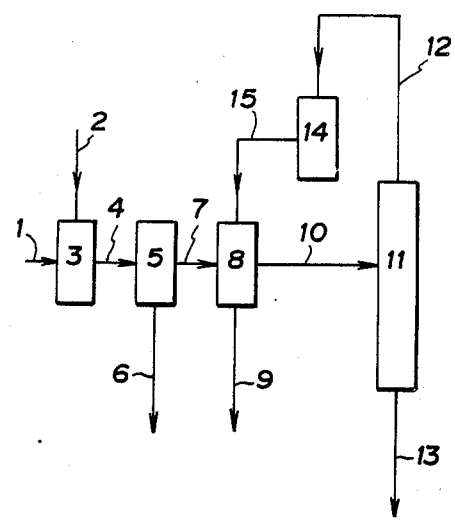
FIG. 1 is a flow diagram illustrating an embodiment of a method for washing the adduct according to the process of this invention.

The present inventors have carried out an intensive investigation for achieving the above objects. As a result, it has been found that the above objects can be achieved by washing the adduct of bisphenol A and phenol with phenol, which is obtained from the decomposed product of an adduct of bisphenol A and phenol. The washed adduct can afford bisphenol A of high purity.

That is, the present invention is a process for preparing 2,2-bis(4-hydroxyphenyl)propane of high purity comprising:

(a) washing an adduct of 2,2-bis(4-hydroxyphenyl)propane and phenol with phenol;

(b) decomposing the washed adduct into 2,2-bis(4-hydroxyphenyl)propane and phenol; and (c) separating the 2,2-bis(4-hydroxyphenyl)propane and phenol wherein the 2,2-bis(4-hydroxyphenyl)propane is recovered and the phonol is used to wash said adduct in step (a).

The invention will be described further in detail.

It has been known to those who are skilled in the art that bisphenol A of high purity can be produced from the adduct of bisphenol A and phenol. However, it has been unknown that the phenol obtained by decomposing the adduct is also highly purified and the purity is higher than any phenol of commercial grade. It has also been unknown that an extremely high purity of the adduct of bisphenol A and phenol be obtained by washing the adduct with phenol thus obtained.

The adducts of bisphenol A and phenol of this invention include, for example, those which are directly obtained from the reaction mixture, those which are obtained by concentrating the filtrate after removing the adduct from the reaction mixture, and those which are obtained by recrystallizing and filtrating the mixture of crude bisphenol A and phenol.

The practical examples of these adducts are those which are obtained by conducting a condensation reaction of acetone and phenol in the presence of hydrochloric acid catalyst, distilling off hydrochloric acid, water and a part of the phenol and cooling the residue, as well as those which are obtained by directly cooling the effluent from a fixed bed reactor containing a cation exchange resin catalyst. The adduct may also be used which is obtained by adding water to a mixture of bisphenol A and phenol, followed by cooling and crystallizing the resultant aqueous mixture as described by Rhone Poulenc Ind. [Japanese Laid-Open Patent TOK-KAISHO 51-91240 (1976)].

Washing of the adduct is conducted in a filter or separator for separating the adduct. As to the washing manner, removal of mother liquor and then washing may be conducted, or removal and washing may be repeated alternately. The adduct discharged from the filter or separator having a small amount of adhered mother liquor may be transferred to an other vessel and washed according to the method of this invention. Furthermore, the washing may also be conducted in the final washing step of a continuously operating centrifuge.

The phenol used for the washing of this invention is obtained as a by-product when the adduct of bisphenol A and phenol is decomposed to give bisphenol A.

Various methods such as distillation, extraction and steam stripping have been proposed to prepare bisphenol A by decomposing the adduct. The phenol used for the washing of this invention may be recovered by any of these methods. The recovered phenol may be used for the washing as it is or after being separated from solvent or water.

The amount of phenol used for the washing of this invention is 0.05 to 0.5 part by weight per part by weight of the adduct of bisphenol A and phenol.

As well known in the art, the mole ratio of phenol to bisphenol A in the adduct is 1:1 and the amount of phenol contained in the adduct is about 30% by weight, which amount is sufficient for use in the final washing of the adduct.

The adduct thus obtained contains almost no impurities both in the crystals and in the adhering washing liquid. Thus the intact bisphenol A obtained by removing phenol can be used as a product or, if necessary, may be further purified or formed prior to use as a product.

The phenol which has been used for the washing of the adduct can be recycled to the reaction or crystallization step in order to recover small amount of bisphenol A which is inevitably dissolved in the phenol.

An example of a flow diagram for carrying out the process of this invention will be briefly described by way of FIG. 1.

A mixture (1) consisting of bisphenol A, phenol and impurities is mixed with water (2) and cooled in the crystallization step (3). The adduct of bisphenol A and phenol is crystallized.

The slurry (4) of crystals thus obtained is transferred to the separation step (5) where crude adduct (7) is separated from the filtrate (6). The crude adduct (7) is washed with phenol (15) in the washing step (8) according to the process of this invention. The washing step may be separate from a separation step or may be a part of the separation step, such as where washing is conducted in a separator.

The washing liquid (9) is recycled to the crystallization step (3). The purified adduct (10) is transferred to the adduct decomposition step (11) and separated into phenol (12) and bisphenol A (13). The intact bisphenol A (13) is a product. Phenol (12) is transferred through the receiver (14) to the washing step (8) of the crude adduct (7).

Figure 2:
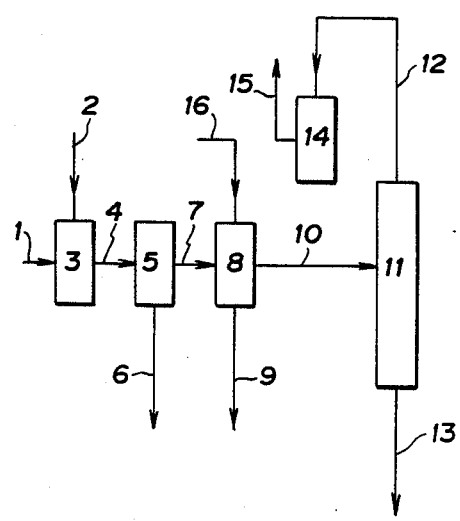
FIG. 2 is a flow diagram illustrating an embodiment of a method for washing the adduct which is not based upon the process of this invention.

FIG. 2 is an example of a flow diagram illustrating a comparative example.

Phenol (15) in the receiver (14) is recovered through the line for using to the reaction. On the other hand, fresh commercial phenol (16) is used for the washing of crude adduct (7).

EXAMPLE

The process of this invention will hereinafter be described in detail by way of the following example and comparative example.

EXAMPLE 1

In FIG. 1, a mixture consisting of 160 kg of bisphenol A, 225 kg of phenol and 15 kg of impurities was fed to the crystallization step at a rate of 400 kg/hr. At the same time, water was fed at a rate of 50 kg/hr. The precipitated amount of the adduct of bisphenol A and phenol was 40 wt. % of the total mixture.

The slurry of the adduct thus obtained was separated in the separation step. The filtrate was transferred to the recovery step. The adduct was transferred to the washing step and washed with phenol at a rate of 18 kg/hr, which phenol had been recovered by decomposing the adduct. The amount of the phenol used for the washing was 0.1 part by weight per part by weight of the adduct.

The adduct thus obtained was fused by heating at 120° C., transferred to the distillation column at a rate of 160 kg/hr and most of the phenol was distilled off at 15 Torr and 170° C. The remaining phenol in the bisphenol A drawn out of the bottom of the column was completely removed by steam stripping to give bisphenol A of high purity. The hue of bisphenol A thus obtained was 10 APHA, and the purity of bisphenol A was satisfactory as a material for preparing optical polycarbonate.

COMPARATIVE EXAMPLE 1

The same procedure described in example 1 was carried out except that the washing was conducted by using commercial phenol according to the process illustrated in FIG. 2. Bisphenol A thus obtained had a hue of 15 APHA. The value was satisfactory for general purposes, but unsatisfactory as a material for preparing optical polycarbonate.

We claim:
1. A process for preparing 2,2-bis(4-hydroxyphenyl)propane of high purity comprising:
   (a) washing an adduct of 2,2-bis(4-hydroxyphenyl)propane and phenol with phenol;
   (b) decomposing the washed adduct into 2,2-bis(4-hydroxyphenyl)propane and phenol by a method selected from the group consisting of distillation, extraction and steam stripping; and
   (c) separating the 2,2-bis(4-hydroxyphenyl)propane and phenol resulting from said decomposition of said washed adduct, wherein 2,2-bis(4-hydroxyphenyl)propane of high purity is recovered and the phenol is used to wash said adduct in step (a).

2. The process of claim 1 wherein the amount of the phenol used for the washing is 0.05 to 0.5 part by weight per part by weight of the adduct of 2,2-bis(4-hydroxyphenyl)propane and phenol.

3. The process of claim 1 wherein the washed adduct is decomposed by distillation.

4. The process of claim 1 wherein the washed adduct is decomposed by extraction.

5. The process of claim 1 wherein the washed adduct is decomposed by steam stripping.

* * * * *